United States Patent [19]

Noe et al.

[11] Patent Number: 4,739,082

[45] Date of Patent: Apr. 19, 1988

[54] ENANTIOMERICALLY PURE MONO ACETAL-PROTECTED DIOLS, THEIR PREPARATION AND USE

[75] Inventors: Christian R. Noe; Max Knollmüller, both of Vienna, Austria

[73] Assignee: Chemie Linz Aktiengesellschaft, Linz, Austria

[21] Appl. No.: 717,383

[22] Filed: Mar. 29, 1985

[30] Foreign Application Priority Data

Apr. 4, 1984 [AT] Austria .................................. 1136/84

[51] Int. Cl.$^4$ .................. C07D 311/00; C07D 311/78
[52] U.S. Cl. .................................. 549/386; 549/397; 549/459
[58] Field of Search .......................... 549/386, 397, 459

[56] References Cited

U.S. PATENT DOCUMENTS 4,497,960 2/1985 Noe ...................................... 549/386
4,609,743 9/1986 Cohen et al. ......................... 549/397

OTHER PUBLICATIONS

Fieser & Fieser, "Lehrbuch der Orgenischen Chemie", Verlag'Chemie, Winheim Bergstr. 4, Auflage 1960, pp. 922–923.
Honben–Weyl, Methoden der Organischen Chemie, Georg Thieme Verlag, Stuttgart, 4, Auflage, Bd. VII, 2a, pp. 610, 611, 615.
Bernardi et al., Synthesis of (+) and (−) Exo and Endo–Brevicomin, Tetrahedron Letters, vol. 22, No. 40 (1981), pp. 4021–4024.
Meyer, Synthesis of Exo–Brevicomin, Liegibs Ann. Chem. (1977), pp. 732–736.
Ferrier et al., Unsaturated Carbohydrates, J. Chem. Soc. Perkin Trans I (1983), pp. 1645–1647.

*Primary Examiner*—Nicky Chan
*Attorney, Agent, or Firm*—Mark Dryer

[57] ABSTRACT

Enantiomerically pure mono acetal-protected diols of the formula

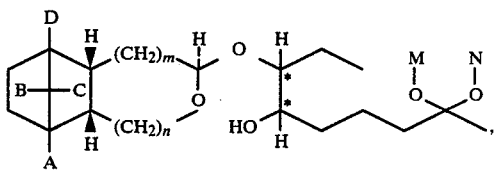

wherein A, B, C and D are hydrogen or a methyl group in any combination, M and N are aliphatic or aralphatic hydrocarbons, m and n are the numbers 0, 1 or 2, whereby the total of m plus n must be the number 1 or 2, their preparation and use for the syntheses of the pheromones (1R-exo)-Brevicomin, (1S-exo)-Brevicomin, (1R-endo)-Brevicomin and (1S-endo)-Brevicomin.

9 Claims, No Drawings

ENANTIOMERICALLY PURE MONO ACETAL-PROTECTED DIOLS, THEIR PREPARATION AND USE

The application relates to enantiomerically pure mono acetal-protected diols, their preparation and use for the synthesis of the pheromones (1R-exo)-brevicomin, (1S-exo)-brevicomin, (1R-endo)-brevicomin and (1S-endo)-brevicomin.

Pheromones are gaining increasing importance in plant protection because of their specifity of action and for environmental reasons. Among others the pheromones of pine beetles, exo-brevicomin and endo-brevicomin have gained particular attention. The pheromone exo-brevicomin acts as an attractant, whereas endo-brevicomin exhibits repellent activity. Brevicomins are chiral structures. This means that there are optical antipodes (=enantiomers). In the case of exo-brevicomin only 1 enantiomer, (1R-exo)-brevicomin, exhibits the desired attractant activity, whereas the other anantiomer is inactive, a phenomenon occuring frequently in physiologically active compounds. Corresponding investigations concerning endo-brevicomin have not yet been published.

Brevicomin is derived from the compound 6,7-dihydoxy-2-nonanone, from which it is obtained by acid catalyzed ring closure. Since 6,7-dihydroxy-2-nonanone has two chiral centres, 4 different brevicomins can result.

They are:

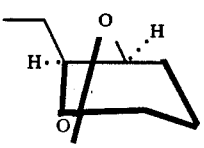
(1S—exo)-Brevicomin

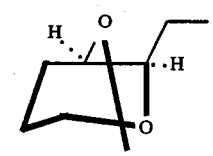
(1R—exo)-Brevicomin

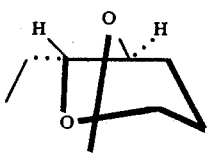
(1S—endo)-Brevicomin

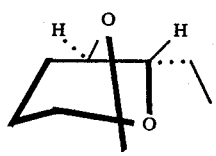
(1R—endo)-Brevicomin

An exactly defined steric arrangement of each of both hydroxy groups is prerequisite to obtain only one of these brevicomins in the cyclisation of 6,7-dihydroxy-2-nonanone. Specific use of protective groups is necessary to achieve this aim. A protected enantiomerically and diastereomerically pure 6,7-dihydroxy-2-nonanone is not known, which exhibits a configuration of the hydroxy groups which leads to only one of both enantiomerically pure endo-brevicomins when the protective group is cleared. Protected 6,7-dihydroxy-2-nonanones which lead to one of the exo-brevicomins are known, they are however not easily accessible in synthesis and in most cases also cleavage of the protective groups is more difficult.

A mixture of exo- and endo-brevicomins can be obtained in a non stereoselective synthesis described by Bernardi, Tetrahedron Letters, Vol. 22, No. 40, pp. 4021–4024 (1981).

Meyer, Liebigs Ann. Chem. 1977, 732–736 describes a multistep synthesis, starting from natural tartaric acid, which leads to biologically inactive (1S-exo)-brevicomin. Compounds from which the endo-brevicomins can be obtained are not described.

According to Ferrier, J. Chem. Soc. Perkin Trans I, 1645–1647 (1983) (1R-exo)-brevicomin is obtained from a dihydroxynonanone, in which both hydroxy groups are protected by benzoyl groups, where however the cleavage of the protective groups and ring closure has to be performed in two steps, alkaline and acidic. Furthermore it is difficult to obtain the protected dihydroxynonanone starting from a selectively protected carbohydrate derivative.

Surprisingly a novel type of compounds of a protected dihydroxynonanone has been found, which is easily accessible in all the four possible configurations of both hydroxy groups. Since in this type of compounds both of the endobrevicomins as well as both exo-brevicomins are selectively preformed concerning their configuration, exactly the corresponding enantiomerically pure brevicomin is formed from the preformed protected dihydroxynonanone by treatment with acid inducing cleavage of the protective group and spontaneous ring closure.

According to this the present invention comprises an enantiomerically pure mono acetal-protected diol of the formula

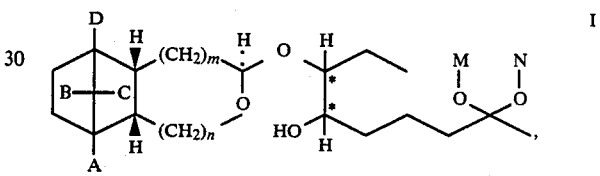

wherein A, B, C and D are hydrogen or a methyl group in any combination, M and N are aliphatic or araliphatic hydrocarbons, m and n are the numbers 0, 1 or 2, whereby the total of m plus n must be the number 1 or 2.

Preferred compounds of the general formula I are compounds in which the bicycloheptane ring system is a bornan ring system (A, B, C=methyl, D=H) since as well the (R)-enantiomers as the (S)-enantiomers of such compounds are relatively easily accessible from readily available natural products (D-camphor, L-borneol). The preferred meaning of n is the number 0. M and N are part of ketone protective groups of the ketal-type, and are aliphatic or araliphatic hydrocarbons. Their preferred meaning is an alkyl group with 1 to 5 carbon atoms or jointly an alkylen group with 2 to 7 carbon atoms, e.g. ethylen or propylen.

A further object of the invention is a process for the preparation of such protected dihydroxynonanones and their use.

The tricyclic acetal protective group is described in U.S. Pat. No. 4,497,960. The starting material of the formula II is synthesized by reaction of racemic 2-hydroxybutanenitrile with an enantiomerically pure anomer selective lactole (or one of its anhydro forms) described in U.S. Pat. No. 4,497,960 and subsequent separation of the diastereomers formed.

The preparation of the novel compounds of the formula I is achieved by reaction of the enantiomerically pure diastereomer of the formula II with a Grignard-compound of the formula III in the presence of a solvent suited for Grignard-reactions e.g. diethylether or tetrahydrofurane at temperatures ranging between about −20° and +30° C. to yield the enantiomerically pure ketone of formula IV. A new chiral centre is formed in the next step, which is the reduction of the keto group to the hydroxy group (formula I). Considerable selectivities can be achieved by choice of the reaction conditions resulting in either cis- or trans arrangement of both hydrogen atoms at the two chiral centres now present.

If complex hydrides, such as lithiumaluminum hydride, sodium-bis-(2-methoxyethoxy)-aluminum hydride or especially zincborohydride, are used in the reduction, the hydrogen atoms predominantly have a cis arrangement relative to each other and endobrevicomin is formed after cleavage of the protective group and ring closure.

The reduction with complex hydrides can be carried out in solvents such as ethers or aromatic hydrocarbons such as toluene. Especially preferred are non-cyclic ethers, such as diethylether or diisopropylether. The range of reaction temperature is between −100° and +40° C.

If the reduction is performed using non complex hydrides, such as borane compounds or alane compounds, e.g. diisobutylaluminum hydride, the hydrogen atomes predominantly have a trans arrangement relative to each other resulting in exo-brevicomin formation after cleavage of the protective group and ring closure.

The choice of solvent is of less influence in the stereoselectivity of the reduction with non complex hydrides. Suited solvents are inert solvents, for example aromatic or aliphatic hydrocarbons e.g. toluene or hexane or cyclic and non cyclic ethers such as tetrahydrofurane or diethylether. The reaction temperatures may vary between −100° and +40° C.

If necessary the diastereomer formed as byproduct can be removed in both modes of reduction. A special advantage is the good separability which may be attributed to the enantiomerically pure tricyclic acetal protective group. The separation is effected preferably by chromatography, however a separation by crystallisation is possible if the diastereomers are crystalline.

The cleavage of all protective groups is performed in one step by addition of catalytic amounts of an acid suited for acetal cleavage such as hydrochloric acid, toluenesulfonic acid, strongly acidic ion exchanger or sulfuric acid, followed by spontaneous ring formation. This cleavage is carried out preferably in the presence of a mercapto acid which reacts with the acetal protective group with preference. Thus a simple purification of the brevicomin is possible by extraction of the thioacetal formed into the alkaline aqueous phase. The tricyclic ring system used as protective group can be easily recovered from this thioacetal by its reaction with methanol to yield the corresponding methylacetal which gives the starting material of the general formula II in the reaction with racemic 2-hydroxybutanenitrile.

EXAMPLE 1

[2R-(2α(R*), 3aα, 4α, 7α, 7aα)]-1-(2-Methyl-1,3-dioxolan-2-yl)-5-[(octahydro-7,8,8-trimethyl-4,7-methanobenzofuran-2-yl)oxy]-heptan-4-one (compound of formula IV, (R))

To a solution of 0,9 g of [2R-(2α(R*), 3aα,4α, 7α, 7aα)]-2-[octahydro-7,8,8-trimethyl-4,7-methanobenzofuran-2-yl)oxy]-butanenitrile (compound of formula II (R)) in dry ether (10 ml) a 1 molar Grignard solution of 2-(3-chloropropyl)-2-methyl-1,2-dioxolane (compound of formula III, X=Cl, 7 ml) in ether is added at 0° C. The mixture is stirred for 3 hr, then petrolether (10 ml) and 10% acetic acid (20 ml) are added, stirred for 10 minutes, extracted with petrolether, the combined organic layers are washed with saturated NaHCO$_3$ solution, dried (Na$_2$SO$_4$) and concentrated in vacuo. The residual oil is purified by column chromatography using triethylamine impregnated silica gel to give the above compound of formula IV (R) (0.93 g, 69%). Coluorless oil, b.p. 100° C./0.005 mm (air bath); $[\alpha]_D^{20}$ = +105.6° (c=1.4 in CH$_2$Cl$_2$); $^1$H-NMR (CDCl$_3$): δ=5.25 (dd, 1H), 4.24 (dd, J$_1$=9.5 Hz, J$_2$=1 Hz; 1H), 4.03 (dd, 1H), 3.92 (s; 4H), 3.2–2.77 (m; 1H), 2.6–2.4 (m; 2H), 2.0–1.2 (m; 13H), 1.31 (s; 3H), 0.92 (t; 3H), 0.98/0.92/0.87 (3s; 9H).

The starting materials of the formula II are prepared in the following manner: A solution of racemic 2-hydroxybutanenitrile (10 g), protecting reagent (19.6 g) and p-toluenesulfonic acid (0.5 g) in dichloromethane (300 ml) is stirred 20 hr at room temperature. After washing with NaHCO$_3$ the solution is dried (Na$_2$SO$_4$) and concentrated in vacuo. The residue is separated by column chromatography using triethylamine impregnated silica gel to give 11.5 g of [2R-(2α(R*)3aα, 4α, 7α, 7aα)]-2-[(oxtahydro-7,8,8-trimethyl-4,7-methanobenzofuran-2-yl)oxy]-butanenitril (compound of formula II (R)) (eluens: petrolether/ether=15:1) and 8.0 g [2R-(2α(S*), 3aα, 4α, 7α, 7aα)]-2-[(octahydro-7,8,8-trimethyl-4,7-methanobenzofuran-2-yl)oxy]-butanenitrile (compound of formula II (S)) (eluens: petrolether/ether=8:1).

Compound of formula II (R): Colourless oil, b.p. 80° C./0.005 mm (air bath); $[\alpha]_D^{20}$ = +201° (c=1.66 in CH$_2$Cl$_2$); $^1$H-NMR (CDCl$_3$): δ=5.52 (d, J=4.4 Hz; 1H), 439 (t, J=6.5 Hz; 1H), 4.17 (d, J=9.3 Hz; 1H), 2.7–3.1 (m; 1H), 2.0–1.1 (m; 9H), 1.05 (t, J=7.4 Hz; 3H), 0.96/0.92/0.87 (3s; 9H).

Compound of formula II (S): Colourless solid, m.p. 56°–57° C.; $[\alpha]_D^{20}$ = +95.3° (c=0.51 in CH$_2$Cl$_2$); $^1$H-NMR (CDCl$_3$): δ=5.38 (d, J=4 Hz; 1H), 4.45 (d, J=9.5 Hz; 1H), 4.14 (t, J=6.5 Hz; 1H), 3.2–2.7 (m; 1H), 1.9–1.2 (m; 9H), 1.05 (t, J=7 Hz; 3H), 1.01/0.93/0.90 (3s; 9H).

EXAMPLE 2

[2R-(2α(S*), 3aα, 4α, 7α, 7aα)]-1-(2-Methyl-1,3-dioxolan-2-yl)-5-[(octahydro-7,8,8-trimethyl-4,7-methanobenzofuran-2-yl)oxy]-heptan-4-one (a compound of formula IV (S))

To a solution of the compound of formula II (S) (1 g), prepared in example 1, in dry ether (10 ml) a 1 molar Grignard solution of 2-(3-chloropropyl)-2-methyl-1,2-dioxolane (compound of formula III) X=Cl, 7.5 ml) in ether is added at 0° C. The mixture is stirred for 3 hr, then petrolether (10 ml) and 10% acetic acid (20 ml) are added and stirring is continued for 10 minutes. After extraction with petrolether, the combined organic layers are washed with saturated NaHCO$_3$ solution, dried (Na$_2$SO$_4$) and concentrated in vacuo. The residue is purified by column chromatography using triethylamine impregnated silica gel (100 g) to give the above compound of formula IV (S) (1.32 g, 88%). Colourless oil, b.p. 110° C./0.01 mm (air bath); $[\alpha]_D^{20}$ = +57.0° (c=2.81 in CH$_2$Cl$_2$); $^1$H-NMR (CDCl$_3$): δ=5.3 (dd, 1H), 4.17 (d, J=11, Hz; 1H), 3.92 (s; 4H), 3.81 (t, J=6.5 Hz; 1H), 3.2–2.8 (m; 1H), 2.6–2.45 (m; 2H), 2.0–1.1 (m; 13H), 1.31 (s; 3H), 0.92 (t, 3H), 0.98/0.90/0.85 (3s; 9H).

EXAMPLE 3

Reduction with DibalH

To a solution of the compound of formula IV (R), prepared in example 1 (2.9 g) in dry toluene (50 ml) a 1.2 molar DibalH solution in n-hexane (10 ml) is added at −60° under $N_2$. After 0.75 hr at −60° the mixture is quenched with 1N NaOH and extracted with ether. The combined organic layers are washed with water, dried ($Na_2SO_4$) and concentrated in vacuo. The residue is separated by column chromatography using triethylamine impregnated silica gel (350 g, eluens: petrolether/ether=1:1) to give 800 mg of [2R-(2α(4R*,5R*), 3aα, 4α, 7α, 7aα)]-1-(2-Methyl-1,3-dioxolan-2-yl)-5-[(octahydro-7,8,8-trimethyl-4,7-methano-benzofuran-2-yl)oxy]-heptan-4-ol (compound of formula I (4R,5R)) and 135 mg of [2R-(2α(4S*,5R*), 3aα, 4α, 7α, 7aα)]-1-(2-Methyl-1,3-dioxolan-2-yl)-5-[(octahydro-7,8,8-trimethyl-4,7-methanobenzofuran-2-yl)oxy]-heptan-4-ol (compound of formula I (4S,5R)). Column chromatography of the fractions containing mixtures of the diastereomeres yields further 920 mg of compound of formula I (4R,5R) and 550 mg of compound of formula I (4S,5R).

Compound of formula I (4R,5R): Colourless oil, b.p. 130° C./0.003 mm (air bath); $[\alpha]_D^{20} = +82.8°$ (c=0.58 in $CH_2Cl_2$); $^1H$-NMR ($CDCl_3$): $\delta=5.43$ (d, J=2.9 Hz; 1H), 4.31 (d, J=9.5 Hz; 1H), 3.93 (s; 4H), 3.7–3.2 (m; 3H), 2.15–1.10 (m; 15H), 1.3 (s; 3H), 1.0 (t, 3H), 0.98/0.92/0.87 (3s; 9H).

Compound of formula I (4S,5R): Colourless oil, b.p. 130° C./0.003 mm (air bath); $[\alpha]_D^{20} = +85.2°$ (c=2.68 in $CH_2Cl_2$); $^1H$-NMR ($CCl_4$): $\delta=5.48$ (d, 1H), 4.29 (d, J=10 Hz; 1H), 3.92 (s; 4H), 3.9–3.45 (m; 2H), 3.2–2.8 (m; 1H), 2.1–1.1 (m; 15H), 1.28 (s; 3H), 0.9 (t; 3H), 0.96/0.90/0.85 (3s; 9H).

Preparation of (1R-exo)-brevicomin

A solution of the above compound of formula I (4R,5R) (330 mg) and 2-mercaptopropanoic acid (352 mg) in dichloromethane is stirred with catalytic amounts of p-toluenesulfonic acid for 1 hour at 20° C. The mixture is extracted with 1N NaOH, the organic layer is dried ($Na_2SO_4$) and concentrated using a Vigreux-column. The residue is distilled to give (1R-exo)-brevicomin (94 mg), $[\alpha]_D^{20} = +83°$ (in ether); $^1H$-NMR ($CDCl_3$): $\delta=4.0$ (broad; 1H), 3.8 (t, J=6.5 Hz; 1H), 1.9–1.4 (m; 8H), 1.3 (s; 3H), 0.88 (t, J=6.8 Hz; 3H).

Preparation of (1S-endo)-brevicomin

A solution of the above compound of formula I (4S,5R) (1.7 g) and 2-mercaptopropanoic acid (1,4 g) in dichloromethane (30 ml) is stirred with catalytic amounts of p-toluenesulfonic acid for 1 hour at 20° C. The mixture is extracted with 1N NaOH, the organic layer is dried ($Na_2SO_4$) and concentrated using a Vigreux-column. The residue is distilled to give (1S-endo)-brevicomin (540 mg), $[\alpha]_D^{20} = -71°$ (in ether); $^1H$-NMR ($CCl_4$): $\delta=4.03$ (broad; 1H), 3.8 (m; 1H), 1.9–1.4 (m; 8H), 1.3 (s; 3H), 0.95 (t; 3H).

EXAMPLE 4

Reduction with Borane in presence of Thiobismethane

To a solution of the compound of formula IV (R), prepared in example 1, (150 mg) in dry ether (5 ml) borane (0.1 ml of a 10M solution in thiobismethane) is added at −55° C. under $N_2$. After 1 hr at −55° C. the mixture is quenched with 1N NaOH, extracted with ether, the combined organic layers are washed with water, dried ($Na_2SO_4$) and concentrated in vacuo. The residue, a mixture of compounds of formula I (4R,5R):I (4S,5R)=3:1, is separated as given in example 3 to give compound of formula I (4R,5R) (95 mg) and compound of formula I (4S,5R) (32 mg).

EXAMPLE 5

Reduction with Lithium aluminum hydride

A solution of the compound of formula IV (R), prepared in example 1 (210 mg) in dry ether (10 ml) is added to lithium aluminum hydride (12 mg) in dry ether (5 ml) at 0° C. under $N_2$. After 15 minutes water is added. The mixture is filtered over hyflo and the organic layer is washed with water, dried ($Na_2SO_4$) and concentrated in vacuo to give a mixture of compounds of formula I (4R,5R):I (4S,5R)=1:2 (205 mg, 97%), which is separated as given in example 3 to give compound of formula I (4R,5R) (61 mg) and compound of formula I (4S,5R) (122 mg).

EXAMPLE 6

Reduction with Sodium bis-2-methoxyethoxy aluminum hydride

To a solution of the compound of formula IV (R), prepared in example 1, (205 mg) in dry ether (5 ml) sodium bis-2-methoxyethoxy aluminum hydride (1.2 mmol) is added at −20° C. under $N_2$. After 0.5 hr the mixture is quenched with 1N NaOH, extracted with ether and the combined organic layers are washed with water, dried ($Na_2SO_4$) and concentrated in vacuo. The resulting mixture (97%) (200 mg) of compounds of formula I (4R,5R) and I (4S,5R) is separated as given in example 3 to give compound of formula I (4R,5R) (51 mg) and compound of formula I (4S,5R) (129 mg).

EXAMPLE 7

Reduction with Zinc borohydride

To a solution of the compound of formula IV (R) prepared in example 1 (220 mg) in dry ether (7 ml) 0.2 molar zinc borohydride (6 ml) is added at 0° C. under $N_2$. After 0.5 hr the mixture is quenched with 1N NaOH and extracted with ether. The combined organic layers are washed with water, dried ($Na_2SO_4$) and concentrated in vacuo to give a mixture of compounds of formula I (4R,5R):I (4S,5R)=1:19 (215 mg, 97%) from which 190 mg of compound of formula I (4S,5R) is isolated as given in example 3.

EXAMPLE 8

Reduction with Zinc borohydride

To a solution of the compound of formula IV (S), prepared in example II, (150 mg) in dry ether (5 ml) 0.2 molar zinc borohydride (4 ml) is added at 0° C. under $N_2$. After 0.5 hr the mixture is quenched with 1N NaOH, extracted with ether, the combined organic layers are washed with water, dried ($Na_2SO_4$) and concentrated in vacuo to give a mixture of the compounds of formula I (4S,5S):I (4R,5S)=1:19 (145 mg, 97%). The compound of formula I (4R,5S) is obtained in pure form by column chromatography: [2R-(2α(4R*,5S*), 3aα, 4α, 7α, 7aα)]-1-(2-Methyl-1,3-dioxolan-2-yl)-5-[(oxtahydro-7,8,8-trimethyl-4,7-methanobenzofuran-2-yl)oxy]-heptan-4-ol: colourless oil, b.p. 130° C./0.003 mm (air bath); $^1H$-NMR ($CDCl_3$): $\delta=5.33$ (dd; 1H), 4.34 (dd, $J_1=1$ Hz, $J_2=8.5$ Hz; 1H), 3.92 (s; 1H), 3.8–3.2

(m; 3H), 3.2–2.7 (m; 1H) 2.1–1.0 (m; 15H), 1.32 (s; 3H), 1.0–0.85 (3H), 0.97/0.92/0.86 (s; 9H).

EXAMPLE 9

Reduction with DibalH

To a solution of the compound of formula IV (S), prepared in example II, (185 mg) in dry ether (7 ml) 1,2 molar DibalH solution in n-hexane (0,5 ml) is added at −60° C. under N$_2$. After 20 minutes at −60° C. the mixture is quenched with 1N NaOH, extracted with ether, the combined organic layers are washed with water, dried (Na$_2$SO$_4$) and concentrated in vacuo to give a mixture of the compounds of formula I (4S,5S):I (4R,5S)=2:1 (180 mg, 97%). The compound of formula I (4S,5S) is obtained in pure form by column chromatography: [2R-(2α(4S*,5S*), 3aα, 4α, 7α, 7aα)]-1-(2-Methyl-1,3-dioxolan-2-yl)-5-[(octahydro-7,8,8-trimethyl-4,7-methanobenzofuran-2-yl)oxy]-heptan-4-ol: colourless oil, b.p. 130° C./0.003 mm (air bath); $^1$H-NMR (CDCl$_3$): δ=5.36 (dd, 1H), 4.36 (d, J=9.3 Hz; 1H), 3.92 (s; 4H); 3.9–2.6 (m; 3H), 2.15–1.10 (m; 16H), 1.32 (s; 3H), 1.0–0.85 (3H), 0.95/0.91/0.86 (s; 9H).

What we claim is:

1. A process for the preparation of enantiomerically pure mono acetal-protected diols of the formula I

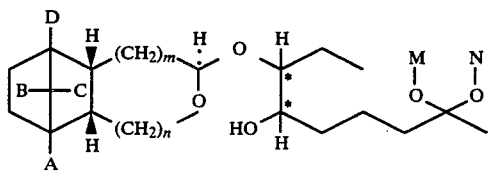

wherein A, B, C and D are hydrogen or a methyl group in any combination, M and N are aliphatic or araliphatic hydrocarbons, m and n are 0, 1 or 2, whereby the sum of m plus n is 1 or 2, comprising reacting (a) an enantiomerically pure acetal-protected 2-hydroxybutane-nitrile of the formula II

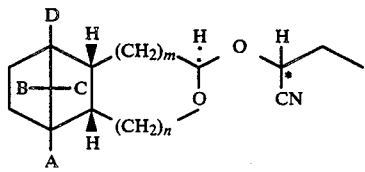

in which A, B, C, D, m and n are as defined above with a Grignard compound of the formula

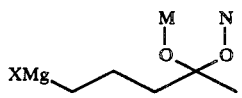

wherein X is chlorine or bromine and M and N are as defined above to the Grignard intermediate, which is hydrolized to the enantiomerically pure ketone of the formula

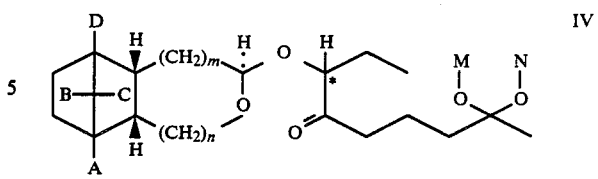

with A, B, C, D, m, n, M, N having the meaning given above (b) and reducing this ketone to the enatiomerically pure mono acetal-protected diastereomer of the formula

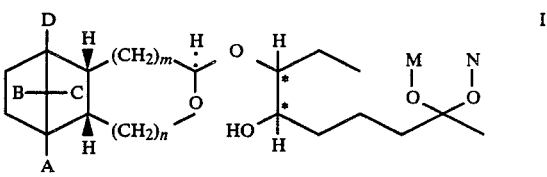

wherein both hydrogen atoms at the chiral centres bearing * have a relative arrangement which is predominantly cis if a complex hydride is used as reducing agent and wherein both hydrogen atoms at the chiral centres bearing * have a relative arrangement which is predominantly trans if a non-complex hydride is used as reducing agent and with or without separating the diastereomer formed as byproduct by using crystallization or chromatography.

2. The processs according to claim 1, comprising reducing the ketone of the formula IV with a complex hydride in the presence of an ether or an aromatic hydrocarbon to an enantiomerically pure compound of the formula I, wherein both hydrogen atoms at the chiral centres bearing * predeominantly have a cis-arrangement, and with or without separating the diastereomer formed as by product by using crystallization or chromatography.

3. The process according to claim 2, wherein the complex hydride is zincborohydride, lithiumaluminumhydride or sodium-bis-(2-methoxyethoxy)-aluminumhydride.

4. The process according to claim 2, wherein the ether is a non cyclic ether.

5. The process according to claim 1, comprising reducing the ketone of the formula IV with a non complex hydride in the presence of an inert solvent to an enantiomerically pure compound of the formula I, wherein both hydrogen atoms at the chiral centres bearing * predominantly have trans-arrangement, and with or without separating the diastereomer formed as byproduct by using crystallization or chromatography.

6. The process according to claim 5, wherein the non complex hydride is a borane or alane compound.

7. A method for the preparation of the enantiomerically pure pheromones (1R-exo)-brevicomin, (1S)-exo)-brevicomin, (1S-endo)-brevicomin and (1R-endo)-brevicomin comprising treating enantiomerically pure diols of the formula I

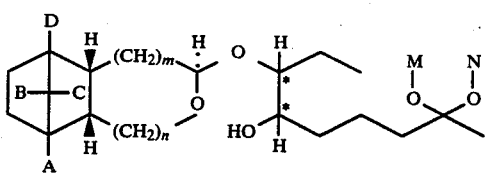

I wherein A, B, C and D are hydrogen or a methyl group in any combination, M and N are aliphatic or araliphatic hydrocarbons and m and n are 0, 1 or 2 whereby the sum of m and n is 1 or 2, with catalytic amounts of a strong acid thereby cleaving the tricyclic acetal-type protective group and the ketone-protective groups and ring closing to form the corresponding enantiomerically pure brevicomin in one step.

8. A method according to claim 7 comprising the treating with a strong acid being carried out in presence of a mercapto acid.

9. A process for the preparation of the enantiomerically pure pheromones (1R-exo)-brevicomin, (1S-exo)-brevicomin, (1S-endo)-brevicomin and (1R-endo)-brevicomin comprising reacting (a) an enantiomerically pure acetal-protected 2-hydroxy-butanenitrile of the formula II

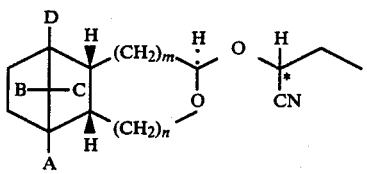

II in which A, B, C and D are hydrogen or methyl groups in any combination and m and n are 0, 1 or 2 whereby the sum of m plus n is 1 or 2 with a Grignard compound of the formula III

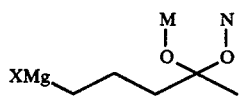

III wherein X is chlorine or bromine and M and N are aliphatic or araliphatic hydrocarbons to the Grignard intermediate which is hydrolized to the enantiomerically pure ketone of the formula IV

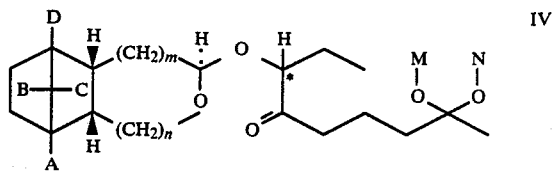

IV with A, B, C, D, m, n, M and N having the meaning given above, (b) reducing this ketone to the enantiomerically pure mono acetal-protected diastereomer of the formula I

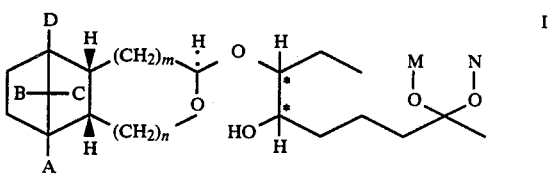

I wherein both hydrogen atoms at the chiral centres bearing * have a relative arrangement which is predominantly cis if a complex hydride is used as reducing agent, and wherein both hydrogen atoms at the chiral centres bearing * have an arrangement which is predominantly trans if a non complex hydride is used as reducing agent, and with or without separating the diastereomer formed as byproduct by using crystalllization or chromatography, (c) and treating the formed enantiomerically pure mono acetal-protected diol of the formula I with catalytic amounts of a strong acid thereby cleaving the tricyclic acetal-protective group and the ketone-protective groups and ring closing to form the corresponding enantiomerically pure brevicomin in one step.

* * * * *